United States Patent
Cramer et al.

(10) Patent No.: US 6,881,540 B2
(45) Date of Patent: Apr. 19, 2005

(54) HIGH THROUGHPUT SCREENING OF POTENTIAL DISPLACER MOLECULES

(75) Inventors: Steven Cramer, Schenctady, NY (US); Kaushal Rege, Troy, NY (US); Jonathan Dordick, Schenectady, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 254 days.

(21) Appl. No.: 09/791,317

(22) Filed: Feb. 23, 2001

(65) Prior Publication Data

US 2001/0047086 A1 Nov. 29, 2001

Related U.S. Application Data

(60) Provisional application No. 60/184,357, filed on Feb. 23, 2000.

(51) Int. Cl.$^7$ .................................................. C12Q 1/68
(52) U.S. Cl. ........................... 435/6; 530/412; 530/415; 530/416; 530/344; 210/198.2; 210/635; 210/656
(58) Field of Search ................................ 530/412, 415, 530/416, 344; 435/6; 210/198.2, 635, 656

(56) References Cited

U.S. PATENT DOCUMENTS

| | | |
|---|---|---|
| 5,478,924 A | 12/1995 | Cramer et al. |
| 5,606,033 A | 2/1997 | Cramer et al. |
| 6,066,848 A * | 5/2000 | Kassel et al. ............. 250/288 |

OTHER PUBLICATIONS

Jayaraman, G.; Yu–Fei, L.; Moore, J. A.; Cramer, S. M. "Ion–exchange displacment chromatography of proteins. Dendritic polymers as novel displacers" Journal of Chromatography A 1995 702(1+2), 143–55.*

* cited by examiner

*Primary Examiner*—Bennett Celsa
*Assistant Examiner*—Jon D Epperson
(74) *Attorney, Agent, or Firm*—Heslin Rothenberg Farley & Mesiti P.C.; Mary Louise Gioeni, Esq.

(57) ABSTRACT

An effective technique for the high throughput screening of displacers is described. In this technique, potential displacers are employed to displace a biomolecule (e.g., protein) adsorbed on a chromatographic resin in small-scale batch displacement experiments. The amount of protein displaced from a specific resin by a defined concentration of displacer is determined by monitoring the supermatant for the protein. By evaluating the displaced protein rather than the displacer itself, this technique enables a single detection technique (e.g., absorbance, fluorescence, etc.) to be employed for all batch displacement experiments. By monitoring the amount of protein displaced, the effacy of a large number of potential displacers can be rapidly evaluated. The entire experimental procedure can be carried out rapidly and is thus amenable to high throughput parallel screening of molecules possessing a large range of affinities and physico-chemical properties. The error of the technique is within 5% of protein displaced, thus making it a very reliable technique. The technique can be extended to different stationary phase materials, biomolecules, and modes of interaction.

12 Claims, 3 Drawing Sheets

Figure1: High throughput screening schematic.
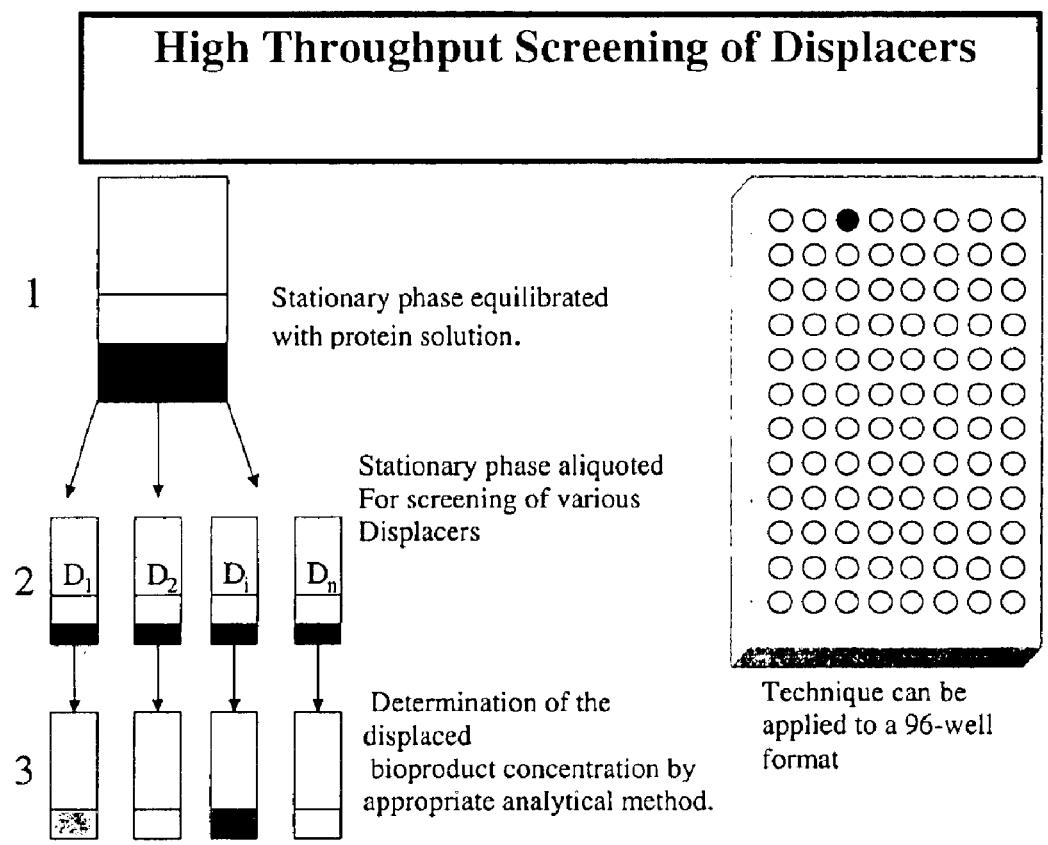

Figure 2: Schematic of the HTS kit.
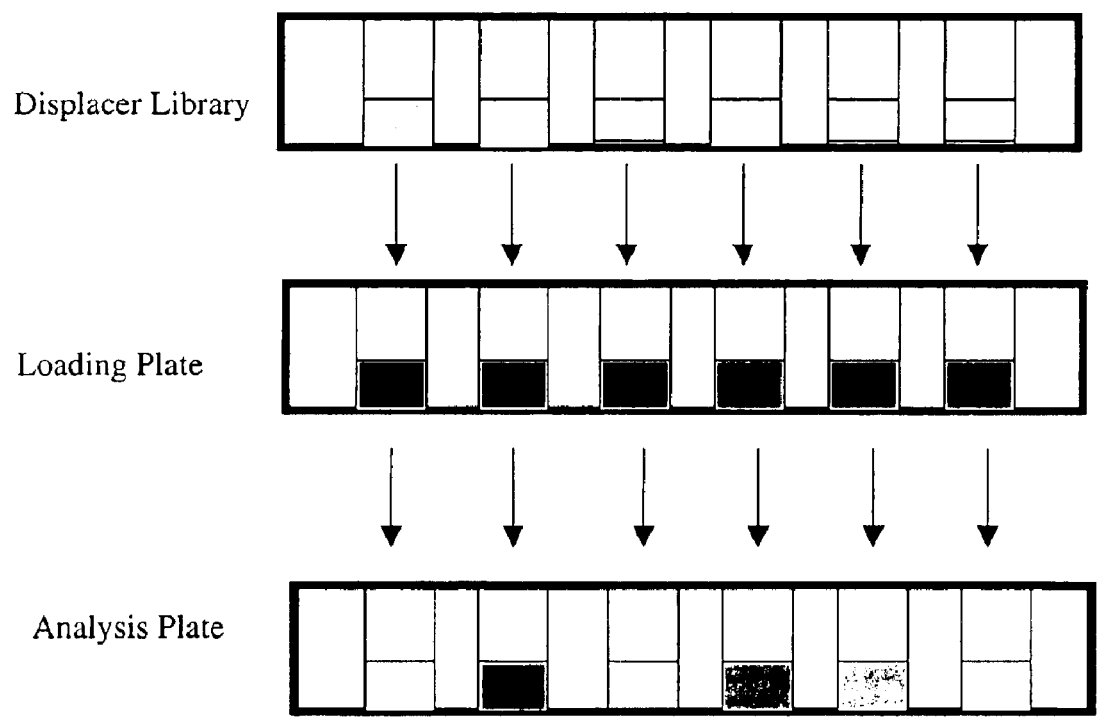

Figure 3: High throughput screening data for Cytochrome C and Lysozyme on H P Sepharose and Toyopearl 550C
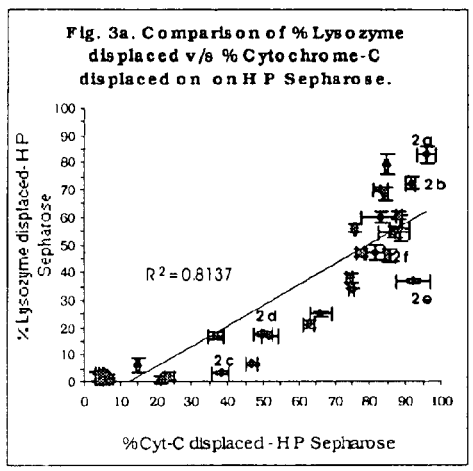
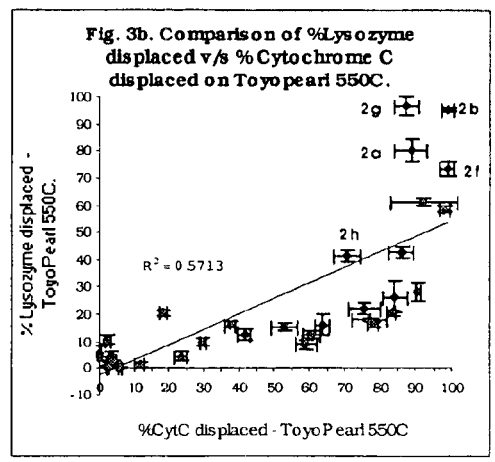
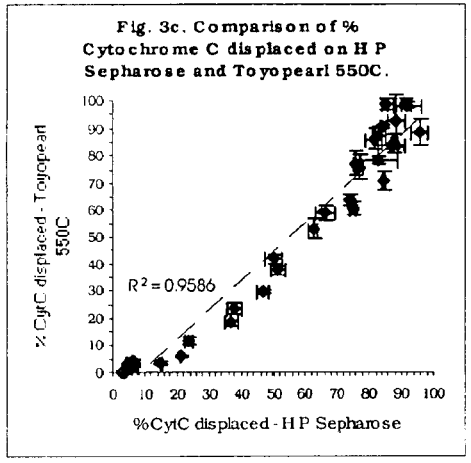
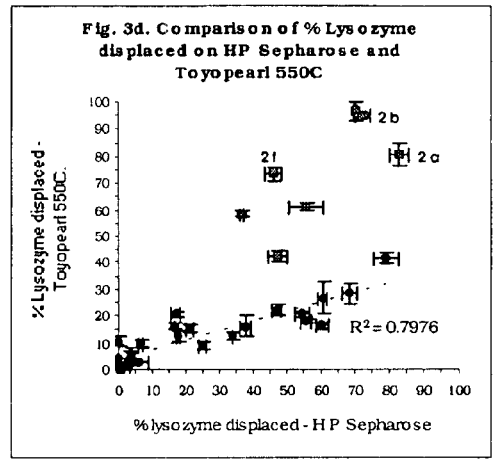

HIGH THROUGHPUT SCREENING OF POTENTIAL DISPLACER MOLECULES

CROSS-REFERENCE TO RELATED APPLICATIONS

This application is a Non-Provisional of a Provisional U.S. Patent Application Ser. No. 60/184,357, filed Feb. 23, 2000, the entire disclosure of which is incorporated herein by reference.

STATEMENT AS TO RIGHTS UNDER FEDERALLY SPONSORED RESEARCH

This invention was made with support from the National Institutes of Health under Grant No. GM47372-04A2. The United States government may have certain rights in the invention.

BACKGROUND OF THE INVENTION

Biological macromolecules such as proteins and polynucleotides have become of increasing commercial interest in medicine as pharmaceutical products. Productivity of synthetic processes is frequently limited by purification methods available. Products of biosyntheses are frequently contaminated by structurally similar impurities that must be removed before the product can be used. Chromatographic methods are typically the most effective purification methods, but the physical and chemical similarities between the desired product and the impurities frequently require laborious multiple separations.

Elution chromatography is the mode almost exclusively known and used. However, a chromatographic system may also be operated in a displacement mode, and operation in this mode can have important advantages for purification of bioproducts, particularly on a preparative and/or an industrial scale. Displacement chromatography is distinguishable from elution chromatography both in theory and in practice. In elution chromatography, a solution of the sample to be purified is applied to a stationary phase, commonly in a column. As the mobile phase is passed over the stationary phase, equilibrium is established between the mobile phase and the stationary phase. Depending on its affinity for the stationary phase, the sample species pass along the column at speeds which reflect their affinity relative to other components that may occur in the original sample.

A modification and extension of isocratic elution chromatography is found in step gradient chromatography wherein a series of eluants of varying compositions are passed over the stationary phase.

Displacement chromatography is fundamentally different from elution chromatography (e.g., linear gradient, isocratic or step gradient chromatography). The displacer, having an affinity higher than any of the feed components, competes effectively for adsorption sites on the stationary phase. An important distinction between displacement and desorption is that the displacer front always remains behind the adjacent feed zones in the displacement train, while desorbents (e.g., salt, organic modifiers) move through the feed zones. The implications of this are quite significant in that displacement chromatography can potentially concentrate and purify components from mixtures having low separation factors. In the case of desorption chromatography, however, relatively large separation factors are generally required to give satisfactory resolution.

In displacement chromatography the eluant (i.e., the displacer) has a higher affinity for the stationary phase than do any of the components in the feed. This is in contrast to elution chromatography, where the eluant usually has a lower affinity. The essential operational feature which distinguishes displacement from elution or desorption chromatography is the use of a displacer molecule. In displacement chromatography, the column is first equilibriated with a carrier solvent under conditions in which the components to be separated all have relatively high binding. The feed solution is then introduced into the column following which the displacer is passed through the column. If the displacer and the mobile phase are appropriately chosen, the products exit the column as adjacent square waves zones of highly concentrated pure material in the order of increasing affinity of adsorption. Following the zones of purified components, the displacer emerges from the column. Finally, after the breakthrough of the displacer, the column is regenerated by desorbing the displacer from the stationary phase to allow the next cycle of operation.

Displacement chromatography has some particularly advantageous characteristics for process scale chromatography of biological macromolecules such as proteins. Displacement chromatography can achieve product separation and concentration in a single step unlike elution chromatography which results in product dilution during separation. Since displacement operates in the non-linear region of the equilibrium isotherm, high column loadings are possible. This allows better column utilization than elution chromatography. Finally, displacement can concentrate and purify components from mixtures having low separation factors unlike the relatively large separation factors which are required for satisfactory resolution in desorption chromatography. Displacement is thus a powerful preparative technique that can offer high production rates, resolving power and elevated yields and purity of a desired byproduct.

The main disadvantage of displacement chromatography, and what has limited its application in bioseparations, is the need to identify a displacer molecule for use in each separation. An effective displacer has greater affinity for the stationary phase than the bioproduct to be purified. Additionally, it should cause separation of the bioproduct from impurities on the column. Finally, it should be readily separable from the bioproduct, so that it does not become an impurity itself.

Identification of an effective displacer has been a laborious and tedious task. Displacer candidates are typically screened individually in column experiments using trial and error. While column experiments indicate the exact behavior of displacer molecules in the column, the time required for screening a large number of molecules is a major limitation. A technique for the high throughput screening of potential displacers would enable rapid screening of molecules generated, for example, from a combinatorial library. Screening of a large number of molecules would also provide sufficient data for a predictive QSAR model to actually direct the design of a displacer molecule for a particular bioproduct or a particular stationary phase. This would enable the identification of important properties for a particular interaction or for similar interactions on different stationary phases. Therefore, a need exists for a rapid method for screening a large number of displacer candidates.

SUMMARY OF THE INVENTION

A rapid method for screening a large number of displacer candidates has been unexpectedly discovered. In this method, a large number of displacer candidates is screened in parallel, enabling extremely rapid assessment of the potential efficacy of each candidate.

In one aspect, then, the present invention relates to a method for screening a plurality of displacer candidates (also called a displacer library, or library of displacers) for efficacy in separating a bioproduct from one or more impurities by means of a displacement chromatography system. The method includes the steps of:

- determining the equilibrium concentration of the bioproduct in the mobile phase solvent, in the presence of the stationary phase resin;
- for each of the displacer candidates, determining the equilibrium concentration of the bioproduct in the mobile phase solvent, in the presence of both the stationary phase resin and the displacer candidate;
- for each of the displacer candidates, determining an amount of the bioproduct displaced from the stationary phase resin; and
- rating each displacer candidate according to a relative amount of the bioproduct displaced from the stationary phase resin.

The step of determining the equilibrium concentration of the bioproduct in the mobile phase solvent, in the presence of the stationary phase resin, includes:

- equilibrating known amounts of the bioproduct, the one or more impurities, the mobile phase solvent and the stationary phase resin;
- performing an analysis of the mobile phase solvent containing the bioproduct, whereby the equilibrium concentration of the bioproduct in the mobile phase solvent, in the presence of the stationary phase resin, is determined.

The step of determining the equilibrium concentration of the bioproduct in the mobile phase solvent, in the presence of both the stationary phase resin and the displacer candidate, includes:

- equilibrating a known amount of each displacer candidate, and known amounts of the bioproduct, the one or more impurities, the mobile phase solvent, the stationary phase resin;
- performing an analysis of the mobile phase solvent containing the bioproduct; and
- whereby the equilibrium concentration of the bioproduct in the mobile phase solvent, in the presence of both the stationary phase resin and a displacer candidate, is determined.

The step of determining an amount of the bioproduct displaced from the stationary phase resin includes:

- finding a difference between an equilibrium amount of bioproduct adsorbed on the stationary phase resin in the presence and in the absence of the displacer candidate.

In addition, a displacer library may be screened for chemical selectivity in displacing the desired bioproduct, while leaving the unwanted impurities bound to a stationary phase resin. In this aspect, the method includes the additional steps of:

- determining the equilibrium concentration of the one or more impurities in the mobile phase solvent, in the presence of the stationary phase resin;
- for each of the displacer candidates, determining the equilibrium concentration of the one or more impurities in the mobile phase solvent, in the presence of both the stationary phase resin and the displacer candidate;
- for each of the displacer candidates, determining an amount of the one or more impurities displaced from the stationary phase resin; and
- rating each displacer candidate according to a relative amount of the bioproduct displaced relative to the amount of the one or more impurities displaced from the stationary phase resin.

In another aspect, the present invention relates to a kit for use in screening a plurality of displacer candidates for efficacy in separating a bioproduct from one or more impurities by means of a displacement chromatography system comprising a mobile phase solvent and a stationary phase resin. The kit includes a displacer library comprising a plurality of displacer candidates and at least one stationary phase resin. It may additionally include a plurality of sample cells, which may be at least one 96-well microtitre plate. A plurality of stationary phase resins may be included in the kit, as well as a mobile phase solvent.

In yet another aspect, the present invention relates to a method for using a kit comprising a plurality of displacer candidates and a stationary phase resin in screening the plurality of displacer candidates for efficacy in separating a bioproduct from one or more impurities by means of a displacement chromatography system. The method includes the steps of:

- combining the stationary phase resin, a mobile phase solvent, and the bioproduct;
- determining the equilibrium concentration of the bioproduct in the mobile phase solvent, in the presence of the stationary phase resin;
- for each of the displacer candidates, combining the stationary phase resin, a mobile phase solvent, the bioproduct and the displacer candidate;
- for each of the displacer candidates, determining the equilibrium concentration of the bioproduct in the mobile phase solvent, in the presence of both the stationary phase resin and the displacer candidate;
- for each of the displacer candidates, determining an amount of the bioproduct displaced from the stationary phase resin; and
- rating each displacer candidate according to a relative amount of the bioproduct displaced from the stationary phase resin.

In yet another aspect, the present invention relates to method for using a chemically selective displacer in separating a bioproduct from one or more impurities. The method includes the steps of:

- dissolving the bioproduct and the one or more impurities in a solvent;
- loading the bioproduct and the one or more impurities, in the solvent, on a chromatographic resin;
- displacing the bioproduct from the chromatographic resin with the chemically selective displacer.

In the method, the one or more impurities are retained on the chromatographic resin. The separation may be by means of a displacement chromatography system, where the solvent is a mobile phase solvent, and the chromatographic resin is a stationary phase resin contained in a displacement chromatography column. A chemically selective displacer may be selected using the screening method of the present invention.

BRIEF DESCRIPTION OF THE DRAWINGS

FIG. 1 is a schematic diagram of a high throughput method for screening displacer candidates according to the present invention.

FIG. 2 is a schematic diagram of a kit according to the present invention containing three 96-well microtitre plates, and its use in automated high throughput screening of a displacer library.

FIGS. 3A–3D are plots of results of high throughput screening of displacer candidates for efficacy in displacing cytochrome C and lysozyme on two different ion exchange resins. Experimental details are described in Example 1.

DETAILED DESCRIPTION OF THE INVENTION

The present invention relates to a method for screening a plurality of displacer candidates for efficacy in separating a bioproduct from one or more impurities, by determining the ability of one or more displacer candidates to displace an adsorbed bioproduct from a stationary phase of a chromatographic system. Bioproducts may be, for example, peptides, proteins, nucleic acids, including olignucleotides, DNA and RNA, polysaccharides, and small molecule natural products and their derivatives. The method may be used with chromatographic systems having different modes of interaction, including ion exchange (IEX), hydrophobic interaction (HIC), and reversed phase (RPLC). Resins useful as a stationary phase for such systems are well known in the art, and are commercially available. Exemplary materials are, for IEX, SP-Sepharose resins available from Amersham Pharmacia, Uppsala, Sweden and Toyopearl ion exchange resins from TosoHaas, Montgomeryville, Pa.; for HIC, the 650M HIC Phenyl, Butyl and Ether series from TosoHaas, and the Phenyl-, Butyl- and Octyl-Sepharose resins from Amersham Pharmacia; and, for RPLC, the Zorbax® series from BTR Separations, Wilmington, Del., Vydac C4, C8 and C18 RPLC columns from Vydac, Hesperia, Calif.; and Octadecyl Silica C18 and Phenyl and Octadecyl resin-based columns from TosoHaas.

A diagram showing the method of the present invention schematically is presented as FIG. 1.

In the method of the present invention, the equilibrium concentration of the bioproduct in a particular mobile phase, in the presence of a particular stationary phase, is determined. For each displacer candidate, the equilibrium concentration of the bioproduct in the same mobile phase, in the presence of the stationary phase and the displacer candidate, is also determined. The displacer candidate is rated according to the relative amount of bioproduct displaced from the stationary phase, which is the difference between the concentration of the bioproduct in the presence of the stationary phase, and the concentration in the presence of both the stationary phase and the displacer candidate.

A solution of the bioproduct, either in pure form, or as an impure mixture, in a solvent appropriate for use as a mobile phase, at an appropriate concentration, 2–10 mg/ml, is typically prepared first. Mobile phase solvents are generally specific to the type of stationary phase used, that is, IEX, HIC, or RPLC, and known in the art. Solvent systems for all three modes are generally aqueous, with additives specific to the type of stationary phase used. For HIC, high salt concentrations are used, and for RPLC, organic modifiers, such as acetonitrile and methanol, are employed. For IEX, aqueous buffers are employed, sometimes with added salt.

A known quantity or amount of the bioproduct is equilibrated with a known quantity of the stationary phase material. Equilibration times typically range from less than two hours to about seven hours. The resulting concentration of the bioproduct in the mobile phase is determined by an appropriate analytical method. Analytical methods that are useful for determining concentration of biological molecules such as the bioproducts are well known. For example, spectrophotometric methods may be used to determine the concentration of a protein, by measuring the fraction of light absorbed at a characteristic wavelength, especially in the visible or UV-visible region of the spectrum. Chromatographic methods, including HPLC and capillary zone electrophoresis (CZE), and other analytical methods, including mass spectrometry and NMR, may be used in place of, or in conjunction with, photometric methods. The amount of bioproduct adsorbed on the stationary phase is then calculated by mass balance.

Concentration of the bioproduct in the mobile phase, in the presence of the stationary phase and the displacer candidate, is also determined. The materials may be mixed in any order, although it is preferable that all mixtures should be prepared by the same method. In one embodiment, a known quantity of a displacer candidate is added to a known concentration of the bioproduct in equilibrium with a known quantity of the stationary phase material. Each displacer candidate is typically dissolved in the mobile phase solvent at a known concentration. In another embodiment, after the stationary phase settles by gravity, most of the solvent containing the bioproduct is decanted, and aliquots of the stationary phase are placed in individual cells for analysis. A known amount of a displacer candidate is then added to each. In yet another embodiment, known quantities of each of the bioproduct, the stationary phase and a displacer candidate are mixed and brought to equilibrium. In all of these embodiments, the equilibrium concentration of the bioproduct is determined, generally by the same analytical method used previously. One advantage of the method of the present invention is that the same analytical method may be used to screen all displacer candidates. The amount of bioproduct adsorbed on the stationary phase in the presence of each displacer candidate is calculated by mass balance and compared to the quantity adsorbed without the displacer. The amount of bioproduct displaced from the stationary phase into the mobile phase, relative to the total amount of bioproduct, may be used as a measure of each displacer candidate's ability to preferentially adsorb on the stationary phase, and, thus, to displace the bioproduct. A displacer is considered potentially useful for a separation if it displaces more than about 50% of the bioproduct. The higher the amount of bioproduct displaced, the more efficacious the displacer will be under column conditions. For example, a compound that displaces 90% of the bioproduct is generally effective over a wide range of column conditions. A compound that displaces less than 50% of the bioproduct may require higher concentrations for a separation to be effected under column conditions. High affinity displacers and the correspondingly lower displacer concentrations made possible thereby typically result in higher yields and higher purity in column experiments. Consequently, a rule of thumb that is generally useful is that an effective displacer displaces at least 70% of the bioproduct under the batch screening conditions.

The present invention also relates to a kit for use in screening a plurality of displacer candidates for efficacy in separating a bioproduct from one or more impurities by means of a displacement chromatography system. The kit includes a displacer library composed of a plurality of displacer candidates, and at least one resin useful as a stationary phase of a displacement chromatography system. Compounds useful as displacer candidates have molecular weight less than 10,000 daltons, preferably less than 5000 daltons, and more preferably less than 2000 daltons; are soluble in aqueous solutions at concentration ranging from 1 mM to 100 mM; and contain both hydrophilic and hydrophobic moieties or substituents. Examples of preferred hydrophilic substituents are sulfate, sulfonate, phosphate, phosphonate, carboxylate and quaternary ammonium groups. Examples of preferred hydrophobic substituents are aromatic, substituted aromatic, aliphatic and substituted aliphatic groups. In particular, displacers useful for separation of proteins by ion exchange displacement chromatography are disclosed in U.S. Pat. Nos. 5,478,924 and 5,606,033, specifically, aminoacids, peptides, nucleic acids, antibiotics, amino- or sulfonate-functional dendrimers, aromatic sulfonic or carboxylic acids, and sulfated sugars. Copending U.S. application, Ser. No. 09/223,090, filing date Dec. 30, 1998, describes use of low molecular weight, surface-active displacers for purification of proteins in hydrophobic interaction and reversed phase liquid chromatographic systems. The kit may also contain a plurality of sample cells for containing the various displacer solutions, and the mixtures of bioproduct, mobile phase solvent and stationary phase resin, with or without a displacer. In particular, the kit may contain one or more 96-well microtitre plates, optionally, prefilled with any or all of a stationary phase resin, a mobile phase solvent, and members of a displacer library.

The method is particularly advantageous in terms of reducing the amount of time required to evaluate a large number of displacer candidates, because the candidates may be screened simultaneously. Even more advantageously, the screening process may be automated, with one or more of the steps carried out automatically. Automated liquid dispensing equipment and analytical and data handling tools may be used to prepare and analyze samples, and to analyze the data produced. For example, wells of multi-assay plates having a quantity of a stationary phase resin disposed within may be charged with a quantity of the bioproduct in solution. Automatic filling equipment may be utilized for this operation, or the charging operations may be performed by a robotic system. Different displacer candidates may then be added to individual wells. Concentration of the bioproduct in the mobile phase, with and without a displacer, may be determined by automated analytical methods. Devices for automatic analysis of the samples include, for example, vertical-beam photometers, wherein the photometer is able to monitor light absorption of samples, contained in wells of a multi-assay plate, at multiple wavelengths, including the visible or UV-visible region of the spectrum, as well as the near-infrared region of the electromagnetic spectrum. Calculation and tabulation of concentrations and relative amount of the bioproduct displaced may be performed using computer software.

A kit according to the present invention may be used in an automated system to screen a plurality of displacer candidates for efficacy in separating a bioproduct from one or more impurities by means of a displacement chromatography system. For example, three 96-well or -channel microtitre plates or units may be included in a kit. Such a kit is illustrated schematically in FIG. 2. Wells in the top unit may contain different displacers, which may be provided as concentrated solutions in appropriate solvents (e.g., water for ion exchange). Buffers may be utilized in the mobile phase to exploit selectivity based on pH, or ionic strength, if desired. In the middle or the loading unit, wells may contain a stationary phase resin. The bottom, or analysis, unit may be used to collect liquid from the top via a suction mechanism. The top and middle units may be provided with a membrane at the bottom of each well to enable liquid flow from the top to the middle unit, and from the middle unit to the bottom unit.

The bioproduct is equilibrated with the resin in the middle unit, and then the mobile phase may be transferred by suction to the bottom unit for analysis. A vertical-beam spectrophotometer may be used to analyze the samples in the bottom unit, quantifying concentration of the bioproduct by absorbance or fluorescence, for example. The amount of bioproduct adsorbed on the resin may then be calculated by mass balance.

A different displacer is then dispensed into each well by means of a robot or a suction mechanism. After equilibration, the supernatant is transferred to the corresponding wells of the analysis unit aligned below. The liquid in the analysis plate is subjected to an appropriate analysis to determine the amount of bioproduct displaced by individual displacers, thus enabling rapid and parallel screening of displacers for the bioproduct of interest.

The method of the present invention may be used to rapidly screen for displacers on stationary phase resins for different modes of chromatography, including ion-exchange, hydrophobic interaction and reversed-phase. The effect of changes in operating conditions, such as ionic strength, pH, and salt and/or organic modifier composition, may also be rapidly determined. Such a multi-dimensional screening process is particularly advantageous in identifying displacers having chemical selectivity under various conditions, to be used as efficient bioseparation agents.

Data generated from screening a large number of displacer candidates according to the method of the present invention may also be used to develop quantitative structure-efficacy relationship (QSER) models. Such models may then be employed in molecular modeling simulations to design more effective displacers for a particular bioproduct. Candidates identified as potentially effective in simulations may then be screened using the method of the present invention, in a repetitive process, leading to development of very efficient displacers for any particular separation.

In another embodiment, the present invention relates to a method for using a chemically selective displacer in separating a bioproduct from an impurity(ies) by means of a displacement chromatography system. A chemically selective displacer is defined as one that displaces the bioproduct from the stationary phase, but leaves the impurity(ies) bound to the stationary phase, or column. The method differs from displacement chromatographic methods currently practiced in that the compound to be purified, the bioproduct, is displaced from the chromatographic resin, either in batch system, or in a column, while the impurity(ies) are retained on the resin. Such a method has obvious advantages in improving both the level of purification possible and the yield of the chromatographic separation.

Steps in the method for using a chemically selective displacer in separating a bioproduct from one or more impurities by means of a displacement chromatography system include dissolving the bioproduct and the one or more impurities in a solvent; loading the bioproduct and the one or more impurities, in the solvent, on a chromatographic resin; and displacing the bioproduct from the chromatographic resin with the chemically selective displacer. The method may be used in a column system where the solvent is a mobile phase solvent, and the chromatographic resin is a stationary phase resin contained in a displacement chromatography column. After the displacer has passed through the column, the impurity(ies) is retained on the stationary phase resin.

The screening method described above may be used to identify chemically selective displacers for a particular separation. In this embodiment of the screening method, the concentration in the mobile phase of both the bioproduct and impurity(ies) is determined, both in the absence and in the presence of the displacer candidate. A rule of thumb that is generally useful is that an effective chemically selective displacer displaces greater than 70% of the bioproduct, and less than 10% of the impurity(ies).

The methods of the present invention may be illustrated with reference to the following examples:

EXAMPLES

Example 1

High Throughput Screening of Displacer Candidates for Protein Separation by Ion Exchange Chromatography Materials:

High Performance S P Sepharose stationary phase material was obtained from Amersham Pharmacia (Uppsala, Sweden). Toyopearl 550 C strong cation exchange resin was obtained from TosoHaas (Montgomeryville, Pa., USA). Phenomenex Jupiter C4 10 μm (250×4.6 mm) column was obtained from Phenomenex, Torrance, Calif., USA.

The potential displacer molecules 2,2 dimethyl-1,3 propanediamine, 3,3'-diamino-N-methyl-dipropylamine, 5-amino-1,3,3-trimethyl cyclohexane methylamine, butylamine, N,N,N', N'-tetrakis(3-aminopropyl)-1,4-butanediamine (DAB(Am)4, polypropyleneaminetetramine dendrimer Gen. 1) diethylenetriamine, hydroxylamine, malonamamidine, malonamide, methylamine, N-methyl 1,3 propanediamine, N,N'bis(2-aminoethyl)-1,3-propanediamine, N,N'bis(3-aminopropyl)1,3-propanediamine, N,N'-diethyl-1,3-propanediamine, N,N'N"-trimethyl bis(hexamethylene) triamine, -2(aminoethyl)-1,3propanediamine, pentaethylene hexamine and tris(2-aminoethyl)amine were purchased from Aldrich (Milwaukee Wis., USA). Bekanamycin sulfate, butirosin disulfate, histamine, lividomycin sulfate, N-α-benzoyl-L-arginine ethyl ester, neomycin sulfate, paromomycin sulfate, sodium phosphate (dibasic), sodium phosphate (monobasic), spermidine and were purchased from Sigma (St. Louis, Mo., USA). 1,2 diaminocyclohexane, cyclohexylamine, piperazine hydrochloride were purchased from TCI America, Portland, Oreg., USA.). Pentaerythrityl (dimethylammonium, cyclohexyl methyl (4)) iodide (PEDMA Cy I(4)), pentaerythrityl (dimethylammonium, benzyl(6)) chloride (PEDMA BzCl(4)), pentaerythrityl (trimethyl ammonium (4)) (PETMA4), dipentaerythrityl trimethyl ammonium 6 (DPE-TMA(6)) were synthesized at Rensselaer [15]. The proteins, horse heart cytochrome-c and chicken egg lysozyme, were purchased from Sigma (St.Louis, Mo., USA).

Equipment:

Absorbance analysis was carried out using a using a Perkin-Elmer Lambda 6.0 UV-Vis Spectrophotometer. (Norwalk, Conn., USA). The chromatographic experiments were carried out using a Waters 600 multisolvent delivery system, a Waters 712 WISP autoinjector and a Waters 484 UV-Vis absorbance detector controlled by a Millenium chromatography software manager (Waters, Milford, Mass.).

Procedures:

High Throughput Screening:

The bulk stationary phase was washed with de-ionized water and then the carrier buffer, 50 mM phosphate, pH 6.0 and allowed to equilibrate for 2 hours. After gravity settling of the stationary phase, the supernatant was removed and 3.0 ml of the remaining stationary phase slurry was combined with a solution (36 ml) containing 3 mg/ml of one of the proteins, cytochrome C or lysozyme, in 50 mM phosphate buffer, pH 6.0, at 20° C. The incubation time for the HP Sepharose and Toyopearl 550C materials were 5 and 7 hours, respectively, in order to attain complete equilibrium. After equilibration was complete, the stationary phase was allowed to gravity-settle and the supernatants were removed and the protein content was determined via UV-VIS absorbance analysis (cytochrome C and lysozyme were evaluated at 540 and 300 nm, respectively). The protein adsorbed on the stationary phase was then determined by mass balance.

Aliquots (25 μl) of the remaining slurry containing the stationary phase resin with the bound protein were then added to a 10 mM solution (300 μl) of one of the displacers in 50 mM phosphate buffer, pH 6.0 at 20° C. Displacers were screened in parallel. A total of 33 different displacers were examined for each protein on each stationary phase material. The system was equilibrated for five (HP Sepharose) or seven (Toyopearl 550C) hours and the experiments were carried out in triplicate. Each displacer, displaced a specific amount of protein from the stationary phase material. When the experiment was complete, the supernatant was removed and the protein content was determined via UV-VIS absorbance analysis as described above. (Note: in order to evaluate these small volumes, 200 μl of the supernatant was diluted to 1.2 ml with the buffer). The concentration of protein was determined and the percentage protein displaced was calculated.

Analytical Chromatography:

Linear gradient reversed phase chromatography using a Phenomenex Jupiter C4, 10 mm; 250 mm×4.6 mm column was used to evaluate the amount of lysozyme in the supernatant for cases where the displacer interfered with the absorbance assay. A linear gradient of 25% to 90% (v/v) buffer B was carried out in 30 minutes (buffer A: 0.1% (v/v) TFA in de-ionized water; buffer B: 90% (v/v) acetonitrile and 0.1% (v/v) TFA in a de-ionized water). The flow rate was 1 ml/min and the column effluent was monitored at 280 nm.

Results obtained with the proteins cytochrome-c and lysozyme on two cation exchange materials (SP-Sepharose HP and Toyopearl 550 C) are presented in Table 1 and FIGS. 3A–3D. Each point on these figures represents a different displacer molecule with the corresponding error bars. The results for the HTS experiments are plotted in the following manner: two proteins on a single resin (FIGS. 3A and B) and one protein on two different resins (FIGS. 3C and D). This is done to enable us to compare the relative efficacy of different displacers for different protein-stationary phase combinations. It is important to note that if the physicochemical phenomena are similar, then the data should be well correlated.

FIG. 3A shows the data for lysozyme and cytochrome-C on SP Sepharose HP. Values for percent protein displaced were consistently higher for cytochrome C than for lysozyme. This is expected since lysozyme is known to be more strongly retained on the SP Sepharose HP material. However, the data is not particularly well correlated ($R^2$= 0.81), indicating that different molecules have various relative efficacies for displacing these two proteins on this resin. Aminoglycosides and highly branched molecules had high efficacy as displacers on Sepharose resin. While, in general, larger molecules with a higher number of charges acted as good displacers for both proteins, an increase in charge did not necessarily imply improved performance as can be seen by comparing the linear molecules N-methyl 1,3 propanediamine (two charges; 46% cytochrome C displaced) and diethylene triamine (three charges; 35% cytochrome C displaced). In addition, it was observed that cyclic molecules had relatively low affinity for displacing lysozyme as compared to cytochrome C on the SP Sepharose material. For example, PEDMACyl$_4$, which has four cyclic groups, displaced 36.7% lysozyme as compared to 91.9% for cytochrome C. Clearly, the presence of significant outliers such as PEDMACyl$_4$ indicates the importance of specific chemistries in determining displacer affinity for a given protein on a specific resin material.

TABLE 1

HTS Data for Cytochrome-C and Lysozyme on HP Sepharose and Toyopearl 550C

| Displacer | CytC on HP Sepharose | Lys on HP Sepharose | CytC on Toyopearl 550C | Lys on Toyopearl 550C |
|---|---|---|---|---|
| Hydroxylamine | 6.23 | 0.43 | 2.25 | 0.00 |
| Histamine | 21.20 | 0.65 | 5.89 | 0.00 |
| Butylamine | 6.72 | 0.00 | 2.16 | 2.07 |
| Malonamide | 3.61 | 0.00 | 0.09 | 4.13 |
| Methylamine | 5.45 | 0.00 | 2.25 | 10.68 |
| 5-amino-1,3,3-trimethyl cyclohexane | 23.63 | 1.94 | 11.52 | 1.38 |
| Cyclohexylamine | 6.23 | 2.59 | 3.90 | 3.10 |
| BAEE | 4.97 | 3.24 | 3.12 | 4.48 |
| Diethylene triamine | 38.11 | 3.67 | 23.38 | 4.48 |
| Malonamamidine | 3.12 | 3.67 | 0.17 | 5.86 |
| Piperazine | 14.93 | 6.26 | 3.55 | 3.10 |
| 2,2 dimethyl-1,3 propanediamine | 46.76 | 6.48 | 29.53 | 9.65 |
| 1,2diaminocyclohexane | 51.71 | 16.85 | 37.50 | 16.19 |
| N-methyl 1,3 propanediamine | 50.06 | 17.71 | 41.65 | 12.40 |
| N,N'-diethyl-1,3 propanediamine | 36.84 | 17.17 | 18.19 | 20.67 |
| N-2(aminoethyl)-1,3propanediamine | 62.60 | 21.17 | 52.83 | 15.16 |
| N,N'bis (2-amino ethyl)-1,3-propanediamine | 66.09 | 25.05 | 59.06 | 8.96 |
| Spermidine | 74.94 | 33.69 | 60.53 | 12.40 |
| Tris(2-aminoethyl) amine | 74.26 | 37.80 | 63.74 | 16.19 |
| Bekanamycin | 75.62 | 55.56 | 76.99 | 18.26 |
| 3,3'-diamino-N-methyl-dipropylamine | 77.17 | 47.09 | 75.60 | 22.05 |
| Butirosin | 83.10 | 60.19 | 78.03 | 16.54 |
| N,N'N"-trimethyl bis(hexamethylene) triamine | 86.89 | 54.43 | 83.22 | 20.67 |
| Pentaethylene Hexamine | 87.86 | 60.48 | 84.09 | 26.53 |
| Paromomycin | 84.17 | 68.47 | 90.41 | 28.25 |
| Neomycin | 95.62 | 82.72 | 88.50 | 80.27 |
| PEDMABzCl4 | 84.95 | 45.95 | 98.70 | 73.37 |
| (DAB(Am)4, polypropylene-aminetertramine Dendrimer | 83.10 | 70.03 | 87.21 | 96.76 |
| DPETMA6 | 91.27 | 72.32 | 98.90 | 95.32 |
| PETMA-4 | 88.35 | 55.64 | 92.23 | 60.87 |
| PEDMA Cyl4 | 91.95 | 36.72 | 98.12 | 58.57 |
| N,N'bis(3-aminopropyl)1,3-propanediamine | 81.45 | 47.09 | 85.91 | 42.38 |
| Lividomycin | 84.61 | 79.17 | 70.49 | 41.34 |

FIG. 3B shows a comparison of the two proteins on TosoHaas Toyopearl 550 C. As with the Sepharose material, the percent protein displaced values for cytochrome C were generally higher than those for lysozyme.

In FIGS. 3C and 3D the displacer efficacies for a single protein on two different resins are examined. FIG. 3C shows the data for cytochrome C. As seen in the figure, when the data is plotted in this manner, it is relatively well correlated (R2~0.96). This indicates that the relative efficacy of different molecules for displacing cytochrome C on these two resins is similar. In other words, the stationary phase effects are not pronounced for the displacement of this particular protein.

On the other hand, when the data for lysozyme displacement is examined (FIG. 3D), there is considerable scatter in the plot. PEDMABzCl4, PEDMACyl4, DABPA4 dendrimer generation 1 (Fix) and neomycin were among the outliers showing significantly higher affinities for displacing lysozyme relative to other displacers. These results indicate that it is possible to design displacers which have chemical selectivity for displacing one protein relative to another on a given stationary phase material. In contrast to the results with SP Sepharose, significant differences in affinity were observed for the aminoglycoside family. While lividomycin and neomycin showed relatively high affinities for displacing both proteins; bekanamycin, exhibited relatively low affinity for displacing lysozyme. These results indicate that molecular size does not play a major role in determining the efficacy of these displacers for lysozyme on this material.

Comparison of displacer efficacies for a single protein, cytochrome C, on two different resins shows the relative efficacy of different molecules for displacing cytochrome C on these two resins is similar. In other words, the stationary phase effects are not pronounced for the displacement of this particular protein. On the other hand, when the data for lysozyme displacement is examined, there is considerable scatter. The major outliers are PEDMABzCl4 (2b), PEDMACyl4, DABPA4 dendrimer generation 1, and neomycin. Clearly, these results indicate that displacers can have significant differences in their efficacy for various stationary phase materials. Further, this data indicates that it is possible to design displacers which are particularly efficacious for a given stationary phase material.

Example 2

High Throughput Screening of Displacer Candidates for Chemically Selective Separation of Proteins by Ion Exchange Chromatography A solution of α-chymotrypsinogen A and Ribonuclease A in 50 mM phosphate buffer, pH 6.0 was prepared to a final concentration of 1.5 mg/ml of each protein. HP Sepharose (3 ml) was washed with the buffer and was equilibrated with 36 ml of protein solution above for four hours. The supernatant was removed and analyzed by linear gradient reversed phase chromatography using UV detection at 280 nm. A portion (25 μl) of the stationary phase resin with the two proteins were transferred to vials. As before, 300 μl of a 10 mM displacer solution were added to each aliquot and the system was allowed to equilibrate for 4 hours at 20° C. The supernatant was analyzed by linear gradient reversed phase chromatography using UV detection at 280 nm. The mass of protein in the supernatant was determined and the percent protein displaced was calculated. Results are shown in Table 2

TABLE 2

HTS data for RNAse A and α-chyA on HP Sepharose.

| | Displacer | α-chyA | RNAse |
|---|---|---|---|
| 1 | BAEE | 1.05 | 3.51 |
| 2 | Malonamamidine | 1.76 | 0.80 |
| 3 | Malonamide | 2.05 | 5.20 |
| 4 | Methylamine | 3.79 | 8.05 |
| 5 | Butylamine | 3.23 | 5.80 |

TABLE 2-continued

HTS data for RNAse A and α-chyA on HP Sepharose.

| Displacer | α-chyA | RNAse |
|---|---|---|
| 6 Hydroxylamine | 4.73 | 10.58 |
| 7 Piperazine | 7.82 | 7.70 |
| 8 Cyclohexylamine | 18.37 | 3.95 |
| 9 N,N'-diethyl-1,3 propanediamine | 28.00 | 55.38 |
| 10 Diethylene Triamine | 28.93 | 57.45 |
| 11 2,2-dimethyl 1,3 propanediamine | 34.78 | 60.45 |
| 12 1,2 diaminocylclohexane | 41.99 | 50.77 |
| 13 N methyl 1,3 propanediamine | 54.07 | 64.29 |
| 14 N(2aminoethylamine)1,3propanediamine | 63.91 | 60.12 |
| 15 Spermidine | 75.31 | 72.29 |
| 16 PETMA4 | 83.45 | 77.30 |
| 17 Pentaethylene Hexamine | 81.14 | 55.30 |
| 18 3,3'diamino-N-methyldipropylamine | 87.33 | 55.61 |
| 19 N,N',N"-trimethylbis(hexamethylene)triamine | 77.73 | 60.19 |
| 20 DPETMA6 | 82.96 | 67.81 |
| 21 Dendrimer | 87.22 | 42.35 |
| 22 Bekanamycin | 82.04 | 53.11 |
| 23 Neomycin | 87.25 | 66.70 |
| 24 Paromomycin | 88.51 | 61.65 |

The table shows that chemically selective displacement is possible using the methods of the present invention.

What is claimed is:

1. A method for extra-column, high throughput, parallel screening of a plurality of displacer candidates for efficacy in separating a bioproduct from one or more impurities by means of a displacement chromatography system comprising a mobile phase solvent and a stationary phase resin, said method comprising:

determining the equilibrium concentration of the bioproduct in at least one first extra-column batch consisting of the bioproduct, the mobile phase solvent, the stationary phase resin, and, optionally, the one or more impurities;

determining the equilibrium concentration of the bioproduct in the mobile phase solvent in a plurality of second extra-column, high throughput, parallel screening batches, each comprising a displacer candidate, the bioproduct, the mobile phase solvent, and the stationary phase resin;

wherein the amount of the bioproduct displaced from the stationary phase resin in each of the plurality of second batches, relative to the total amount of the bioproduct bound in the first batch, is an indicator of the efficacy of the displacer contained therein.

2. A method of screening a plurality of displacer candidates according to claim 1, wherein determining the equilibrium concentration of the bioproduct in the first extra-column batch comprises:

equilibrating known amounts of the bioproduct, the one or more impurities, the mobile phase solvent and the stationary phase resin, and, optionally, the one or more impurities; and performing an analysis of the mobile phase solvent containing the bioproduct; and whereby the equilibrium concentration of the bioproduct in the mobile phase solvent, in the first extra-column batch, is determined.

3. A method of screening a plurality of displacer candidates according to claim 1, wherein determining the equilibrium concentration of the bioproduct in the mobile phase solvent in the plurality of second batches comprises:

equilibrating a known amount of each displacer candidate, and known amounts of the bioproduct, the one or more impurities, the mobile phase solvent, the stationary phase resin; and performing an analysis of the mobile phase solvent containing the bioproduct; and whereby the equilibrium concentration of the bioproduct in the mobile phase solvent, is determined.

4. A method of screening a plurality of displacer candidates according to claim 1, wherein the amount of the bioproduct displaced from the stationary phase resin is determined by finding a difference between an equilibrium amount of bioproduct adsorbed on the stationary phase resin in the presence and in the absence of the displacer candidate.

5. A method of screening a plurality of displacer candidates according to claim 1, wherein the stationary phase resin is an ion exchange resin.

6. A method of screening a plurality of displacer candidates according to claim 1, additionally comprising:

determining the equilibrium concentration of the one or more impurities in the mobile phase solvent, in the presence of the stationary phase resin;

for each of the displacer candidates, determining the equilibrium concentration of the one or more impurities in the mobile phase solvent, in the presence of both the stationary phase resin and the displacer candidate;

for each of the displacer candidates, determining an amount of the one or more impurities displaced from the stationary phase resin; and rating each displacer candidate according to a relative amount of the bioproduct displaced relative to the amount of the one or more impurities displaced from the stationary phase resin.

7. A method for high throughput, parallel extra-column screening of a plurality of displacer candidates for efficacy in separating a bioproduct from one or more impurities by means of a displacement chromatography system comprising a mobile phase solvent and a stationary phase resin, said method comprising:

determining the equilibrium amount of the bioproduct adsorbed on the stationary phase resin in a first extra-column batch consisting of a known amount of the bioproduct, the mobile phase solvent, a known amount of the stationary phase resin, and, optionally; the one or more impurities;

determining the equilibrium amount of the bioproduct adsorbed on the stationary phase resin in each of a plurality of second extra-column high throughput, parallel screening batches comprising a known amount of a displacer candidate, a known amount of the bioproduct, the mobile phase solvent, and a known amount of the stationary resin;

calculating the amount of the bioproduct displaced from the stationary phase resin in each of the plurality of second batches;

wherein the amount of the bioproduct displaced from the stationary phase resin in each of the plurality of second batches, relative to the total amount of the bioproduct in each batch, is an indicator of the efficacy of the displacer contained therein.

8. A method according to claim 7, wherein the equilibrium amount of the bioproduct adsorbed on the stationary phase in the first extra-column batch comprises:

equilibrating known amounts of the bioproduct, the one or more impurities, the mobile phase solvent and the stationary phase resin;

performing an analysis of the mobile phase solvent containing the bioproduct; and calculating the equilibrium amount of the bioproduct adsorbed on the stationary phase resin.

9. A method according to claim 7, wherein determining the equilibrium amount of the bioproduct adsorbed on the stationary phase in each of the plurality of second extra-column high throughput, parallel screening batches comprises:

equilibrating a known amount of each displacer candidate with known amounts of the bioproduct, the one or more impurities, the mobile phase solvent, the stationary phase resin;

performing an analysis of the mobile phase solvent containing the bioproduct; and calculating the equilibrium amount of the bioproduct adsorbed on the stationary phase resin.

10. A method according to claim 7, wherein the amount of the bioproduct displaced from the stationary phase resin in each of the plurality of second batches is determined by calculating the difference between the equilibrium amount of bioproduct adsorbed on the stationary phase resin in the presence and in the absence of the displacer candidate.

11. A method according to claim 7, wherein the stationary phase resin is an ion exchange resin.

12. A method according to claim 7, additionally comprising:

determining the equilibrium amount of the one or more impurities adsorbed on the stationary phase resin in each of the plurality of second extra-column high throughput, parallel screening batches;

calculating the amount of the one or more impurities displaced from the stationary phase resin in each of the plurality of second batches.

* * * * *

UNITED STATES PATENT AND TRADEMARK OFFICE
CERTIFICATE OF CORRECTION

PATENT NO.   : 6,881,540 B2
DATED        : April 19, 2005
INVENTOR(S)  : Cramer et al.

It is certified that error appears in the above-identified patent and that said Letters Patent is hereby corrected as shown below:

Column 14,
Line 61, insert the word -- resin -- after the word "phase".

Column 15,
Line 5, insert the word -- resin -- after the word "phase".

Signed and Sealed this

First Day of November, 2005

JON W. DUDAS
*Director of the United States Patent and Trademark Office*